(12) United States Patent
Li et al.

(10) Patent No.: US 7,883,688 B2
(45) Date of Patent: Feb. 8, 2011

(54) POLYCATIONIC POLYROTAXANES CAPABLE OF FORMING COMPLEXES WITH NUCLEIC ACIDS

(75) Inventors: Jun Li, Singapore (SG); Chuan Yang, Singapore (SG); Hongzhe Li, Singapore (SG); Xin Wang, Singapore (SG); Suat Hong Goh, Singapore (SG); Kam W. Leong, Ellicott City, MD (US)

(73) Assignees: Agency for Science, Technology and Research, Singapore (SG); National University of Singapore, Singapore (SG)

( * ) Notice: Subject to any disclaimer, the term of this patent is extended or adjusted under 35 U.S.C. 154(b) by 220 days.

(21) Appl. No.: 11/347,001

(22) Filed: Feb. 3, 2006

(65) Prior Publication Data

US 2006/0211643 A1 Sep. 21, 2006

Related U.S. Application Data

(60) Provisional application No. 60/649,715, filed on Feb. 3, 2005.

(51) Int. Cl.
*A61B 5/055* (2006.01)
*C12N 5/00* (2006.01)
*C12N 5/02* (2006.01)
*A61K 48/00* (2006.01)

(52) U.S. Cl. .................. 424/9.35; 435/320.1; 514/44 R
(58) Field of Classification Search .................. None
See application file for complete search history.

(56) References Cited

U.S. PATENT DOCUMENTS

| | | | | |
|---|---|---|---|---|
| 5,691,316 | A | 11/1997 | Agrawal et al. | 514/44 |
| 5,824,470 | A * | 10/1998 | Baldeschwieler et al. | 435/6 |
| 5,855,900 | A | 1/1999 | Nobuhiko | 424/425 |
| 6,113,880 | A * | 9/2000 | Platzek et al. | 424/9.35 |
| 6,828,378 | B2 * | 12/2004 | Okumura et al. | 525/55 |
| 7,297,348 | B2 | 11/2007 | Li et al. | 424/485 |
| 7,309,500 | B2 * | 12/2007 | Kim et al. | 424/489 |
| 7,417,110 | B2 | 8/2008 | Wang et al. | 528/398 |
| 7,612,142 | B2 * | 11/2009 | Ito et al. | 525/54.4 |
| 7,622,527 | B2 * | 11/2009 | Ito et al. | 525/54.4 |
| 2002/0019369 | A1 | 2/2002 | Li et al. | 514/59 |
| 2003/0008818 | A1 | 1/2003 | Pun et al. | 514/12 |
| 2009/0004741 | A1 | 1/2009 | Wang et al. | 435/455 |
| 2009/0012027 | A1 | 1/2009 | Wang et al. | 514/44 R |

FOREIGN PATENT DOCUMENTS

WO   WO 2004/009664   1/2004

OTHER PUBLICATIONS

Deonarain (1998) Expert Opin. Ther. Pat., 8: 53-69.*
Verma (1997) Nature, 389: 239-242.*
Eck et al. (1996) Goodman & Gilman's The Pharmacological Basis of Therapeutics, McGraw-Hill, New York, NY., pp. 77-101.*
Gorecki (2001) Expert Opin. Emerging Drugs 6(2): 187-98.*
Ooya, et al. (2004) Science and Technology of Advanced Materials, 5: 363-69.*
Lee and Kim (2003) Rotaxane Dendrimers, Dendrimers V: Functional and Hyperbranched Building Blocks, Photophysical Properties, Applications in Materials and Life Sciences, 228: 111-140, Published by Springer-Verlag, Berlin, DE.*
Dvornikovs, et al. (2003) Journal of the American Chemical Society, 125: 8290-301.*
Ooya, et al. (1994) Science and Technology of Advanced Materials, 5(3): 363-69.*
Huh, et al. (2001) Macromolecules, 34: 2402-04.*
Nepogodiev, et al. (1998) Chemical Reviews, 98: 1959-76.*
Rao, et al. (2004) Expert Opinion in Biological Therapy, 4(4): 507-18.*
Kihara, et al. (2002) Bioconjugate Chemistry, 13: 1211-19.*
Ooya, T. and Yui, N. (1999) "Polyrotaxanes: Synthesis, Structure, and Potential in Drug Delivery", Critical Reviews in Therapeutic Drugs Carrier Systems, 16(3): 289-330.*
Schlager, et al. (1999) Cytotechnology, 30(1-3), pp. 71-80.*
Morrison and Boyd's "Organic Chemistry, 3rd Ed.", Published by Allen and Bacon, Needham Heights, MA., 1965, pp. 602-603.*
Harada, A., et al., "The Molecular Necklace; a Rotaxane Containing Many Threaded α-Cyclodextrins," *Nature*, 356:325-327 (1992).
Harada, A., et al., "Double-stranded Inclusion Complexes of Cyclodextrin Threaded on Poly(ethylene-glycol)," *Nature*, 370:126-128 (1994).
Leong, K.W., et al., "DNA-polycation nanospheres as non-viral gene delivery vehicles," *J. Controlled Rel.* 53:183-193 (1998).
Luo, D, et al., "Synthetic DNA Delivery Systems," *Nature Biotechnol.*, 18:33-37 (2000).
Li, J., et al., "Inclusion Complexation and Formation of Polypseudorotaxanes between Poly[(ethylene-oxide)-ran-(propylene oxide)] and Cyclodextrins," *Macromolecules*, 34:8829-8831 (2001).
Li, J., et al., "Preparation and Characterization of Polypseudorotaxanes based on block-selected inclusion complexation between poly(propylene oxide)-poly(ethylene oxide)-poly(propylene oxide) triblock copolymers and cyclodextrin," *J. Am. Chem. Soc.* 125:1788-1795 (2003).
Li, J. et al., "Preparation and Characterization of Inclusion Complexes formed by Niodegradable poly (ε-caprolactone) triblock colopymer and cyclodextrins," *Polymer*, 45:1777-1785 (2004).
Niidome, T., et al., "Gene Therapy Progress and Prospects; Nonviral Vectors," *Gene Therapy*, 9:1647-1652 (2002).
Wenz, G., et al. "Threading cyclodextrin rings on polymer chains," *Angew. Chem. Int. Ed.*, 31:19-199 (1992).

(Continued)

*Primary Examiner*—Robert M Kelly
(74) *Attorney, Agent, or Firm*—K & L Gates LLP; Stephanie Seidman; Frank J. Miskiel

(57) ABSTRACT

A polycation capable of forming a complex with a nucleic acid for carriage thereof. The polycation comprising at least one cyclic compound having a cavity. A polymer backbone is threaded into the cavity of the cyclic compound. A pair of bulky moieties cap the terminals of the polymer backbone to inhibit dethreading of the cyclic compound from the polymer backbone. In use, the net positive charge of said polycation enables a complex to form with nucleic acid.

14 Claims, 19 Drawing Sheets

OTHER PUBLICATIONS

Choi et al., "Preparation and characterization of polypseudorotaxanes based on biodegradeable Poly(L-lactide)/poly-(ethylene glycol) triblock copolymers," Macromolecules 36:9313-9318 (2003).

Fujita et al., "Thermally Induced Localization of Cyclodextrins in a Polyrotaxane Consisting of $^\beta$-Cyclodextrins and Poly(ethylene glycol)-Poly(propylene glycol) Triblock Copolymer," Macromolecules 32:2534-2541 (1999).

Fujita et al., "Synthesis and characterization of a polyrotaxane consisting of $^\beta$-cyclodextrins and a poly(ethylene glycol)-poly(propylene glycol) triblock copolymer," Macromol. Chem. Phys. 200:706-713 (1999).

Fujita et al., "Thermally-Responsive Properties of a Polyrotaxane Consisting of β-Cyclodextrins and a Poly(ethylene glycol)-Poly(propylene glycol) Triblock-Copolymer," Polymer Journal 31(11-2):1099-1104 (1999).

Hood et al., "Tumor regression by targeted gene delivery to the neovasculature," Science 296:2404-2407 (2002).

Ikeda et al., "Supramolecular network formation through inclusion complexation of an α-cyclodextrin-based molecular tube," J. Phys. Chem. B 107:14-19 (2003).

Ikeda et al., "Supramolecular network formation through inclusion complexation of an a-cyclodextrin-based molecular tube," Macromol. Rapid Commun. 21:1257-1262 (2000).

Kircheis et al., "Tumor-targeted gene delivery: an attractive strategy to use highly active effector molecules in cancer treatment," Gene Therapy 9:731-735 (2002).

Li et al., "Block-selected molecular recognition and formation of polypseudorotaxanes between poly(propylene oxide)-poly(ethylene oxide)-poly(propylene oxide) triblock copolymers and alpha-cyclodextrin," Angew. Chem. Int. Ed. Engl. 43:3215 (2004).

Li et al., "Cationic Supramolecules Composed of Multiple Oligoethylenimine-Grafted β-Cyclodextrins Threaded on a Polymer Chain for Efficient Gene Delivery," Adv. Mater. 18:2969-2974 (2006).

Li et al., "Cyclodextrin-based supramolecular architectures: syntheses structures, and applications for drug and gene delivery," Adv. Drug. Deliv. Rev. 60: 1000-1017 (2008).

Li et al., "Drug carrier systems based on water-soluble cationic beta-cyclodextrin polymers," Int. J. Pharm. 278: 329-342 (2004).

Li et al., "Self-assembled supramolecular hydrogels formed by biodegradable PEO-PHB-PEO triblock copolymers and alpha-cyclodextrin for controlled drug delivery," Biomaterials 27: 4132-4140 (2006).

Li et al., "Targeted gene delivery to pulmonary endothelium by anti-PECAM antibody," Am J Physiol Lung Cell Mol Physiol 278: L504-L511 (2000).

Ooya, T. and N. Yui, "Multivalent interactions between biotin-polyrotaxane conjugates and streptavidin as a model of new targeting for transporters," J Control Release 80(1-3):219-228 (2002).

Schiffelers et al., "Cancer siRNA therapy by tumor selective delivery with ligand-targeted sterically stabilized nanoparticle," Nucleic Acids Research 32(19): e149, pp. 1-10 (2004).

Wang et al., "Synthesis and characterization of cationic micelles self-assembled from a biodegradable copolymer for gene delivery," Biomacromolecules 8: 1028-1037 (2007).

White et al., "Targeted gene delivery to vascular tissue in vivo by tropism-modified adeno-associated virus vectors," Circulation 109: 513-519 (2004).

Yang et al., "Cationic supramolecules consisting of oligoethylenimine-grafted alpha-cyclodextrins threaded on poly(ethylene oxide) for gene delivery," J. Biomed. Mater. Res. A: Apr. 10, 2008.

Harada et al., "Complex formation between polyisobutylene and cyclodextrins: inversion of chain-length selectivity between β-cyclodextrin and γ-cyclodextrin," Macromol 26(19):5267-5268 (1993).

Harada et al., "Formation of inclusion complexes of monodisperse oligo(ethylene glycol)s with α-Cyclodextrin," Macromol 27(16):4538-4543 (1994).

Harada et al., "Preparation and characterization of a polyrotaxane consisting of monodisperse Poly(ethylene glycol) and α-Cyclodextrins," J Am Chem Soc. 116(8):3192-3196 (1994).

Harada et al., "Preparation and characterization of inclusion complexes of poly(propylene glycol) with cyclodextrins," Macromol 28(24):8406-8411 (1995).

Harada et al., "Preparation and characterization of polyrotaxanes containing many threaded α-cyclodextrins," J Organic Chem 58(26):7524-7528 (1993).

Harada et al., "Preparation and properties of inclusion complexes of polyethylene glycol with α-cyclodextrin," Macromol 26(21):5698-5703 (1993).

Li et al., "Formation of supramolecular hydrogels induced by inclusion complexation between pluronics and α-Cyclodextrin," Marcromol 34(21):7236-7237 (2001).

Li et al., "Injectable drug delivery systems based on supramolecular hydrogels formed by poly(ethylene oxide)s and α-cyclodextrin," J Biomedical Mater Res A. 65A(2):196-202 (2003).

Li, X. and K. Leong, "Preparation and characterization of inclusion complexes of biodegradable amphiphilic poly(ethylene oxide)—Poly[(R)-3-hydroxybutyrate]—Poly(ethylene oxide) Triblock Copolymers with Cyclodextrins," Macromol 36(4):1209-1214 (2003).

Zhao et al., "Fabrication of novel supramolecular hydrogels with high mechanical strength and adjustable thermosensitivity," J Phys Chem 110:16503-16507 (2006).

Liu et al., "Threading α-Cyclodextrin through Poly[(R,S)-3-hydroxybutyrate] in Poly[(R,S)-3-hydroxybutyrate]—Poly(ethylene glycol)—Poly[(R,S)-3-hydroxybutyrate] Triblock Copolymers: Formation of Block-Selected Polypseudorotaxanes" Macromolecules 41(16):6027-6034 (2008).

Ma et al., "UV photopolymerized hydrogels with β-cyclodextrin moieties" J. Polymer Res. 15(4):301-307 (2008).

Ni et al., "Supramolecular hydrogels based on self-assembly between PEO-PPO-PEO triblock copolymers and alpha-cyclodextrin." J. Biomed. Mater. Res. A. 88(4):1031-6 (2009).

Wu et al., "Synthesis of supramolecular nanocapsules based on threading of multiple cyclodextrins over polymers on gold nanoparticles" Angew. Chem. Int. Ed. Engl. 48(21):3842-3845 (2009).

Yang et al., "A supramolecular gene carrier composed of multiple cationic α-cyclodextrins threaded on a PPO-PEO-PPO triblock polymer" Polymer 50(6):1378-1388 (2009).

Yang et al., "Cationic Polyrotaxanes as gene carriers: Physicochemical properties and real-time observation of DNA complexation, and gene in cancer cells" J. Phys. Chem. B 113(22):7903-7911 (2009).

Yang et al., "Cationic star polymers consisting of alpha-cyclodextrin core and oligoethylenimine arms as nonviral gene delivery vectors" Biomaterials 28(21):3245-3254 (2007).

Yang et al., "Cationic supramolecules consisting of oligoethylenimine-grafted alpha-cyclodextrins threaded on poly(ethylene oxide) for gene delivery" J. Biomed. Mater. Res. A. 89(1):13-23 (2009).

Yang et al., "Novel supramolecular block copolymer: A polyrotaxane consisting of many threaded α- and γ-cyclodextrins with an ABA triblock architecture" Macromolecules 42(12):3856-3859 (2009).

Yang et al., "Synthesis and characterization of polyrotaxanes consisting of cationic alpha-cyclodextrins threaded on poly[(ethylene oxide)-ran-(propylene oxide)] as gene carriers" Biomacromolecules 8(11):3365-74 (2007).

Yang et al., "Thermoresponsive behavior of cationic polyrotaxane composed of multiple pentaethylenehexamine-grafted alpha-cyclodextrins threaded on poly(propylene oxide)-poly(ethylene oxide)-poly(propylene oxide) triblock copolymer" J. Phys. Chem. B 113(3):682-690 (2008).

Zhang et al., "Pseudo-Block Copolymer Based on Star-Shaped Poly(N-isopropylacrylamide) with a β-Cyclodextrin Core and Guest-Bearing PEG: Controlling Thermoresponsivity through Supramolecular Self-Assembly" Macromolecules 41(16):5967-5970 (2008).

* cited by examiner (I)

POLYCATIONIC POLYROTAXANES CAPABLE OF FORMING COMPLEXES WITH NUCLEIC ACIDS

REFERENCE TO RELATED APPLICATION

This application claims priority to U.S. Provisional Application No. 60/649,715 filed on Feb. 3, 2005. The disclosure of the above application is incorporated herein by reference in its entirety.

TECHNICAL FIELD

The present invention generally relates to polycations that form complexes with nucleic acid for transfection into a target cell.

BACKGROUND

The ability to deliver DNA to target cells has been playing a key role in the development of new approaches, such as gene therapy and DNA vaccination, for treating and controlling diseases. DNA delivery systems have been classified as viral and non-viral vector systems. Although viral vectors are highly efficient at delivering DNA into cells, their routine uses in clinic and basic research laboratories have been limited because of, inter alia, their high toxicity, restricted targeting of cells, limited DNA carrying capacity, production and packaging problems, recombination, and high cost.

Non-viral vectors, the majority of which are synthetic gene carrier systems, have advantages in terms of simplicity of use, ease of large-scale production, and lack of specific immune response.

The use of polymers for carriage of DNA carrier is a promising non-viral gene delivery approach, most of which is composed of cationic polymer segments that form a condensed complex with DNA to protect DNA against digestion by enzymes. The condensed polymer-DNA complex also packs into compact and small nano-particles, which can be internalized by cells through endocytosis process and transferred through the diverse barriers toward the nucleus of the target cell, where the gene can be expressed.

Cationic polymers of linear, branched, star and dendritic structures have been studied as DNA condensation agents in the context of non-viral gene delivery. Controlled chemical synthesis of cationic polymers ensures that the size and shape of the polymers are consistent and defined, thereby improving the reproducibility of NDA delivery. Polyethyleneimine (PEI) is one of the most frequently studied polycations for this application. The size and the structure of PEI have strongly influenced the efficiency of gene transfer technologies with regard to transfection activity and cytotoxicity. Generally, low molecular weight branched PEI ($\leqq$2000 Da) proved to be nontoxic but displayed very poor transfection activity. By contrast, high molecular weight branched PEI ($\leqq$25 kDa) showed high transgene expression but also significant cytotoxicity. In the intermediate molecular weight range (2000-25 kDa), the PEI is of medium to low cytotoxicity and also medium transfection activity. Furthermore, no matter what the molecular weight is or whether the cationic polymers are linear, branched, star, or dendrimers, they are mostly non-biodegradable, which may cause sustained damage for the cells after the gene delivery.

There is a need to provide polycations that overcome or at least ameliorate one or more of the disadvantages described above.

SUMMARY

According to a first aspect of the invention, there is provided a polycation for carriage of a nucleic acid comprising:
at least one cyclic compound having a cavity;
a polymer backbone threaded into the cavity of said cyclic compound;
a pair of bulky moieties capping the terminals of said polymer backbone to inhibit dethreading of said cyclic compound from said polymer backbone,
wherein, the net positive charge of said polycation enables a complex to form with said nucleic acid.

Advantageously, the polycation is useable as a transfection agent for transfecting an exogenous nucleic acid into a target cell. More advantageously, the bulky moieties are biocleavable in that they are linked to said polymer backbone by biodegradable linkages so that said bulky moieties are degraded in vivo and thereby cleaved from said polymer backbone.

In one embodiment, there is provided a polycation for transfection of nucleic acid into a cell, the polycation comprising:
a polymer backbone threaded into the cavity of a plurality of amine-substituted cyclodextrins; and
a pair of biocleavable bulky moieties capping the terminals of said polymer backbone to inhibit dethreading of said cyclodextrins from said polymer backbone,
wherein, the degree of amino-substitution of said cyclodextrins enables said polycation to form a complex with said nucleic acid.

According to a second aspect, there is provided a composition for introducing an exogenous nucleic acid molecule into a target cell, comprising a polycation having at least one cyclic compound having a cavity;
a polymer backbone threaded into the cavity of said cyclic compound;
a pair of bulky moieties capping the terminals of said polymer backbone to inhibit dethreading of said cyclic compound from said polymer backbone,
wherein, the net positive charge of said polycation enables a complex to form with said nucleic acid.

According to a third aspect, there is provided a method for introducing an exogenous nucleic acid molecule into a target cell comprising the steps of:
forming a complex between a polycation and a nucleic acid, the polycation having at least one cyclic compound having a cavity;
a polymer backbone threaded into the cavity of said cyclic compound;
(a) a pair of bulky moieties capping the terminals of said polymer backbone to inhibit dethreading of said cyclic compound from said polymer backbone; and
(b) introducing said formed complex to a target cell.

The target cell may be an in vitro or in vivo target cell

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 5(a): is aminated alpha-cyclodextrin (negative control); FIG. 5(b) is a complex of the polycation of example 1 and DNA; and FIG. 5(c) is a complex of the polycation of Example 1 and DNA;

DEFINITIONS

Figure 1:
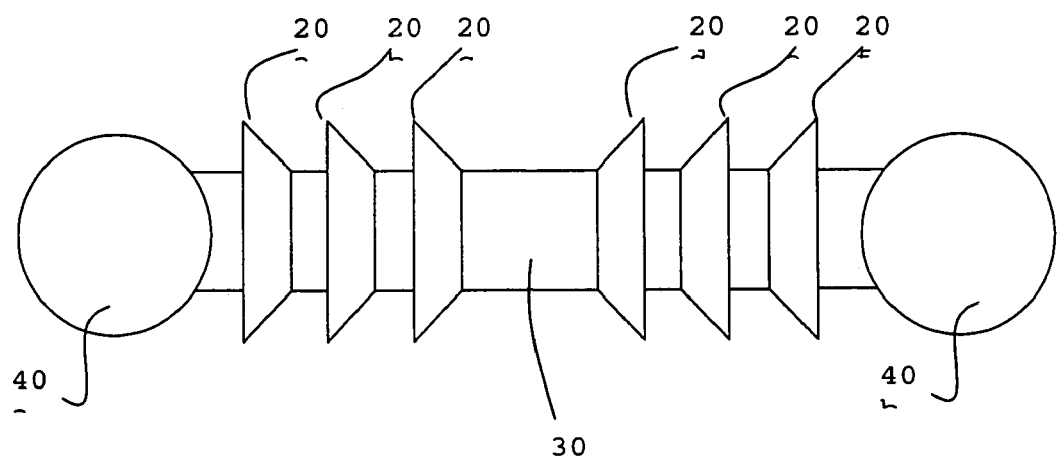
FIG. 1 shows a schematic view of a polyrotaxane polycation.

The following words and terms used herein shall have the meaning indicated:

The terms "cyclic compound", "cyclic molecule" and grammatical variations thereof means a molecule that is cyclic in that it has a ring structure and also to a molecule which is of a substantial ring structure. That is, the term "substantial ring" means to include molecules in which the ring is not closed completely, as in the letter "C", and molecules having a helical structure in which as in the letter "C", one end and the other end are not connected and placed in a piled manner.

The term 'amphiphilic' denotes a molecule combining hydrophilic and hydrophobic properties.

The term "amine-substituted cyclic compound" refers to a cyclic compound having at least one attached amine group. Likewise, the term "amine-substituted cyclodextrins" refers to a cyclodextrin compound having at least one attached amine group.

The term "amine group" refers to primary, secondary and tertiary amine groups as well as groups derived from amine groups, such as imine groups.

The term "nucleic acid", and equivalent terms such as polynucleotide, refers to a polymeric form of nucleotides of any length, such as ribonucleotides, deoxyribonucleotides or peptide nucleic acids (PNAs), that comprise purine and pyrimidine bases, or other natural, chemically or biochemically modified, non-natural, or derivatized nucleotide bases. The nucleic acid may be double stranded or single stranded. References to single stranded nucleic acids include references to the sense or antisense strands. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The terms nucleoside, nucleotide, deoxynucleoside and deoxynucleotide generally include complements, fragments and variants of the nucleoside, nucleotide, deoxynucleoside and deoxynucleotide, or analogs thereof.

As used herein, the term recombinant refers to a compound or composition produced by human intervention.

As used herein, a "recombinant" nucleic acid or protein molecule is a molecule where the nucleic acid molecule which encodes the protein has been modified in vitro, so that its sequence is not naturally occurring, or corresponds to naturally occurring sequences that are not positioned as they would be positioned in a genome which has not been modified.

The term "transfection" as used herein refers to the process of introducing nucleic acids into a host cell.

As used herein, the term "transfection agent" is meant refer to an agent that promotes and facilitates the uptake of nucleic acid by the cells.

The term "transfection efficiency" refers to the percentage of target cells, within a population of target cells, that contain an introduced exogenous nucleic acid molecule.

The term "introducing" when used in reference to an exogenous nucleic acid molecule, means that the nucleic acid molecule is delivered into a target cell; i.e., the nucleic acid molecule is transfected into the target cell.

The term "target cell" is used herein to mean any cell into which an exogenous nucleic acid molecule is to be introduced.

Unless specified otherwise, the terms "comprising" and "comprise", and grammatical variants thereof, are intended to represent "open" or "inclusive" language such that they include recited elements but also permit inclusion of additional, unrecited elements.

The term "branched" polymer is meant to designate a polymer having side chains or branches which are bonded to the polymer backbone.

The term "star polymer" is used to describe polymer molecule structures that have multiple arms extending generally from a central core.

The term "bulky moieties" and grammatical variations thereof refers to any substituents group that has sufficient bulk to substantially inhibit dethreading of said cyclic compounds from the chain of said polymer.

The terms "biocleavable linkage", "biocleavable linker" "biodegradable linker", "biodegradable linkages" and grammatical variations thereof are defined as types of specific chemical moieties or groups used within the polycation that couple and optionally cross-link a bulky moiety to the polymer backbone and which, in vivo, and preferably during or after transfection, cleave the bulky moieties from said polymer backbone.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DISCLOSURE OF EMBODIMENTS

Exemplary, non-limiting embodiments of a polycation for carriage of a nucleic acid will now be disclosed.

The nucleic acid comprises at least one and preferably a plurality of cyclic compounds having cavities. The plurality of cyclic compounds being threaded through their cavities by a polymer backbone. The terminals of the polymer backbone being capped with groups having sufficient bulk to substantially inhibit dethreading of the cyclic compounds. In use, the net positive charge of said polycation enables a complex to be formed with the nucleic acid.

The polymer backbone may be selected from the group consisting of linear polymers, branched polymers, star polymers and combinations thereof.

The polymer backbone may be a hydrophilic or hydrophobic polymers.

Exemplary polymers are selected from the group consisting of polyethylene glycol, polypropylene glycol, polybutylene glycol, polypentylene glycol, polyhexylene glycol, polymethyl vinyl ether, polyethyl vinyl ether, polyisoprene, polyisobutylene, polybutadiene, and copolymers thereof. In one embodiment the polymer is a poly(ethylene glycol), a derivative thereof, or a copolymer that reacts with the poly (ethylene glycol) segment. The polymer can also be poly (propylene glycol) or other poly(alkylene glycols). Higher molecular weight poly(ethylene glycol) is also called poly (ethylene oxide). The copolymer may be any one of a variety of biodegradable and biocompatible copolymers that contain ethylene glycol units which can form hydrogels with cyclodextrins such as polyesters, polyurethanes, polyamides, polyethers, polysaccharides, poly(amino acids), polypeptides, or a protein. Modified poly(ethylene glycol) may be also be used, such as pegylated polysaccharides, pegylated polyaminoacids, and pegylated proteins. The poly(ethylene glycol) derivatives or copolymers may have poly(ethylene glyol) or polypropylene oxide) segment(s) at the end(s), in which the middle segment carries positive charge.

The polymer backbones may have molecular weights of about 200 to about 50000, about 200 to about 10000, about 200 to about 5000, about 200 to about 2000.

The plurality of cyclic compounds may comprise one or more cyclodextrins. Cyclodextrins are a series of natural cyclic oligosaccharides composed of six, seven, eight, or more D (+) glycopyranose units linked by α-1,4 linkages. Advantageously, cyclodextrins are biodegradable and biocompatible in vivo.

The cyclodextrins may be selected from the group consisting of α-cyclodextrins, β-cyclodextrins, γ-cyclodextrins, hydroxypropylated α-cyclodextrin, hydroxypropylated β-cyclodextrin, and hydroxypropoylated γ-cyclodextrin, dimethylcyclodextrin.

Other cyclic compounds that may be used include crown ethers, cyclofructan and combinations thereof.

Optionally, the cyclodextrins are naturally occurring cyclodextrins or modified cyclodextrins comprising one or more substituents groups. The modified cyclodextrins may be synthesized cyclodextrins and may be synthesized naturally by microorganisms, for example.

The modified cyclodextrins may be substituted with one or more nucleophilic groups. the nucleophilic groups may have the general formula of:

where R is optional and is an aliphatic hydrocarbon radical and x is 0=<x<3.

In one embodiment, the nucleophilic groups may be amine groups. The amine groups may be selected from the group having the following formula: —N, —NH, and —NH$_2$. The amine substituents groups may substitute one or more hydroxyl groups of said cyclodextrins.

In one embodiment, the number of amine substituent groups on one of said cyclodextrins may be selected from the group consisting of: 1, 2, 3, 4, 5, 6, 7, 8, 9, 10, 11, 12, 14, 15, and 16.

More advantageously, in one embodiment, the plurality of cyclic compounds are substituted with one more nucleophilic groups to enhance the ability of the polycation to form a complex with said nucleic acid.

Advantageously, the polymeric assembly is a supramolecular polymeric assembly (polyrotaxne) and, without being bound by theory, it is believed that the nucleic acid is held by the net positive charge of said polycation and in particular the nucleophilic substituted cyclic groups. Advantageously, the nucleic acid is bound to a biodegradable polymeric assembly and is released not by a process of cleavage of individual polymer-nucleic acid linkages but by a process wherein the biodegradation at selected sites to break down the entire assembly in a controlled manner. This allows the entire nucleic acid carried by the polymeric assembly to be released into a target cell as the polymeric assembly is dissociated in the body of a patient.

In one embodiment, the number of cyclodextrins on one polymer backbone may be selected from the group consisting of: 1, 2, 3, 4, 5, 6, 7, 8, 9, 10, 11, 12, 14, 15, and 16.

In one embodiment, the polycation comprises:
polyethylene glycol polymer threaded into the cavities of at least 6 cyclodextrins having at least one amine substituents group thereon; and
a pair of biocleavable bulky moieties capping the terminals of said polyethylene glycol polymer.

In one embodiment, there are between 6 to 8 cyclodextrins having 4 to 6 substituent amine groups thereon; and
a pair of biocleavable bulky moieties capping the terminals of said polyethylene glycol polymer.

The bulky moieties may be either one of a group having at least one benzene ring or a group having at least one tertiary butyl. Exemplary groups that have at least one benzene ring include benzyloxycarbonyl (Z) group, 9-fluorenylmethyloxycarbonyl (Fmoc) group, and benzyl ester (OBz) group. Exemplary groups that have at least one tertiary butyl include benzyloxycarbonyl group, tertiary butylcarbonyl (Boc) group and amino acid-tertiary butyl ester (OBu) group.

The bulky moieties may be connected to the straight chain-polymer backbone by a biocleavable linker. The biocleavable linker may be selected from the group consisting of amides, amines and lower alkyls having from 1 to about 8 carbon atoms such as methyl, ethyl and propyl, esters having from 1 to about 8 carbon atoms such as phosphate ester and orthoester, phosphazene and anhydrides.

In one embodiment, the polycation is made according to the step of:

(a) threading a polymer backbone through the cavity of a plurality of cyclodextrins.

The method may further comprise the step of:

(b) adding an amine group to said plurality of cyclodextrins to thereby

In another embodiment, the cyclodextrins are aminated with one or more of the amine substituents groups before being threaded by the polymer backbone.

EXAMPLES

Non-limiting examples of the invention, and a comparative example will be further described in greater detail by reference to specific Examples, which should not be construed as in any way limiting the scope of the invention.

Referring to FIG. 1, there is shown a schematic view of a polyrotaxane molecule 10. The polyrotaxane molecule 10 has a plurality of cyclic molecules (20a-f) having structural cavities through which a linear molecule 30 is threaded and acts as the "axis". At the terminal end of the linear molecule are a pair of blocking groups (40a,40b) which prevent the dethreading of the cyclic molecules 20a-f.

Figure 2:
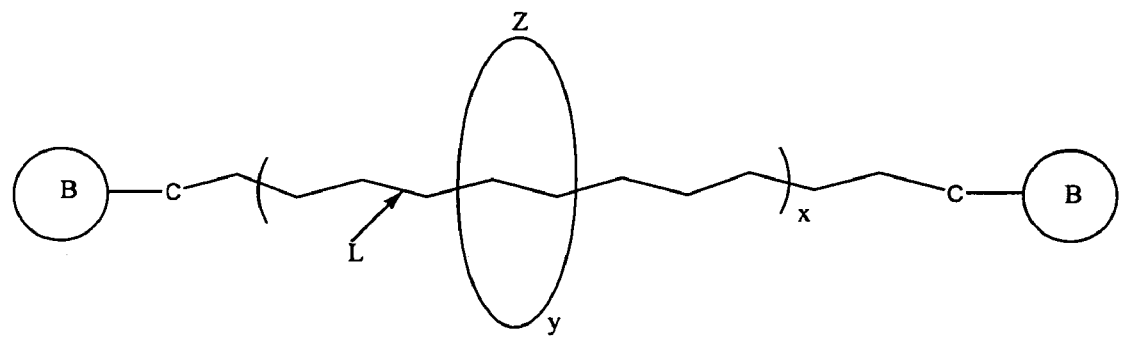
FIG. 2 shows a schematic view of a polyrotaxane polycation of general formula (I)

Referring now to FIG. 2, there is shown a schematic view of a polyrotaxane polycation of general formula (I) wherein L represents a polymer backbone of which there are x repeating monomer units. Z represents cyclic compounds having cavities that are threaded by the polymer backbone L. The cyclic compounds Z may have an optional glucose moiety, wherein y represents the ratio of the optional glucose side chains to the cyclic compounds. A pair of bulky moieties B capping the terminal ends of the polymer backbone L to inhibit dethreading of the cyclic compounds Z. The bulky moieties B are coupled to the polymer backbone by biocleavable linkers C.

In one embodiment, L is polyethylene glycol. In one embodiment, x is a value from about 3 to about 100

In one embodiment, y is a value in the range selected from the group consisting of ⅙ to about 1, . . . ⅐ to about 1, and ⅛ to about 1.

In one embodiment, the linkers c are selected from the group consisting of —NH, —NCH$_2$NHCO—.

In one embodiment, the cyclic compound Z is a cyclodextrin selected from the group consisting of α-cyclodextrins, β-cyclodextrins, and γ-cyclodextrins.

In one embodiment, the cyclodextrin comprising a plurality of aminated D-glucose units. In one embodiment, the cyclodextrin comprised about 5 to about 8, more preferably about 6 to about 7, aminated D-glucose units. The α-cyclodextrins may comprise from 1 to 6 aminated D-glucose units. The β-cyclodextrins may comprise from 1 to 7 aminated D-glucose units. The γ-cyclodextrins may comprise from 1 to 8 aminated D-glucose units. The aminated D-glucose units may be represented by the general formula (II):

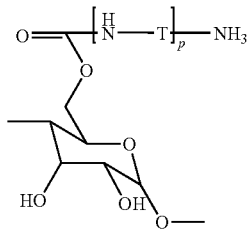

wherein p is an integer from 0 to about 8, or 0 to 1 to 4, and wherein T is optional and is an alkyl selected from the group consisting of methyl (—CH$_3$), ethyl (—CH$_2$CH$_3$) and propyl (—CH$_2$CH$_2$CH$_3$). In one embodiiment, p=5. In one embodiment, T is ethyl (—CH$_2$CH$_3$).

Example 1

Preparation of End-Capped Polyrotaxane with Alpha-Cyclodextrin and Poly(Ethylene Glycol)

Amino-terminated PEG 3350 (0.335 g) was added to 33 ml (0.145 g/ml) of α-cylodextrin (α-CD) saturated aqueous solution (purchased from Tokyo Kasei Inc, Japan) in a centrifuge tube. The tube was sonicated in a water bath for 20 min followed by stirring overnight at 4° C.

The inclusion complex formed as a white precipitate and was isolated by centrifugation before being dried in vacuum to yield 3.677 g of polypseudorotaxane.

2,4-Dinitrofluorobenzene (11.43 g, 61.4 mmol) was dissolved in 3 ml of anhydrous N,N-dimethylformamide (DMF). The solution was slowly added to 3.677 g of the polypseudorotaxane while stirring. After the addition was completed, 7 ml more anhydrous DMF was added drop wise, and the mixture was stirred overnight at room temperature. The reaction mixture was poured into 300 ml of MeOH, and the precipitate was centrifuged and washed with methanol (MeOH) 3 times.

The resulting product was further dissolved in 15 ml of Dimethyl sulfoxide (DMSO), and poured into 300 ml of de-ionised (DI) water before being centrifuged and then washed a second time with DI water.

Figure 3:
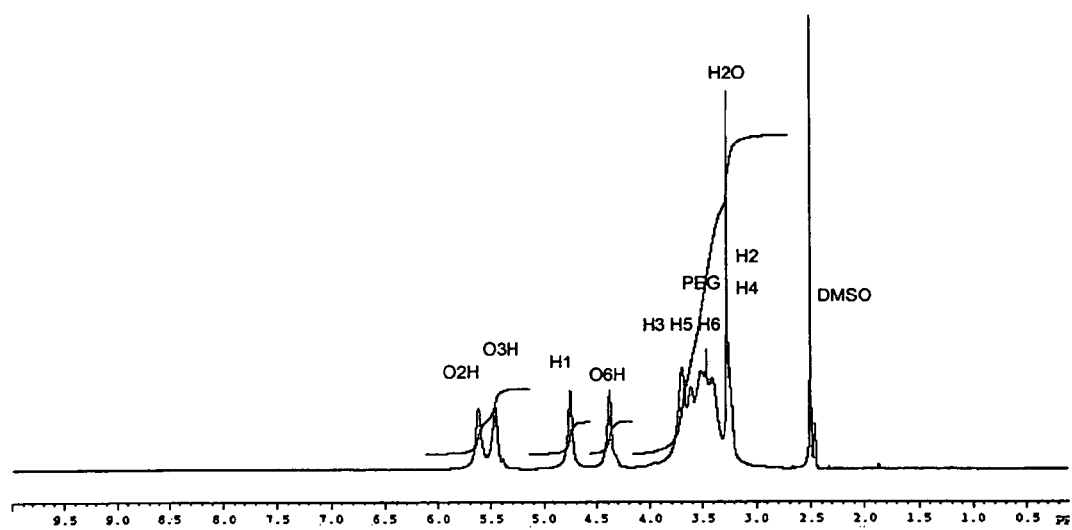
FIG. 3 shows the 1H NMR spectrum in DMSO-d6 of the polyrotaxane polycation disclosed in Example 1.

The final product was freeze-dried to yield 0.658 g of a pure polyrotaxane (here called "polyrotaxane-1"), the $^1$H NMR spectrum of which is shown in FIG. 3.

Example 2

Preparation of Aminated Polyrotaxane with Alpha-Cyclodextrin Grafted with Ethylene Diamine 0.162 g (0.00912 mmol) of the polyrotaxane-1 was heated overnight to 40° C. under vacuum to remove all traces of water. After cooling down to room temperature, the polyrotaxane-1 was dissolved in 40 ml of dry DMSO under a N2 atmosphere. The solution was added dropwise to 1.92 g (11.81 mmol) of N, N'-carbonyldiimidazole (CDI) in 40 ml dry DMSO, and reacted overnight under N2 atmosphere. The resulting solution was poured into THF/Et2O. The CDI-activated polyrotaxane was precipitated and centrifuged, and further washed with THF.

Figure 4:
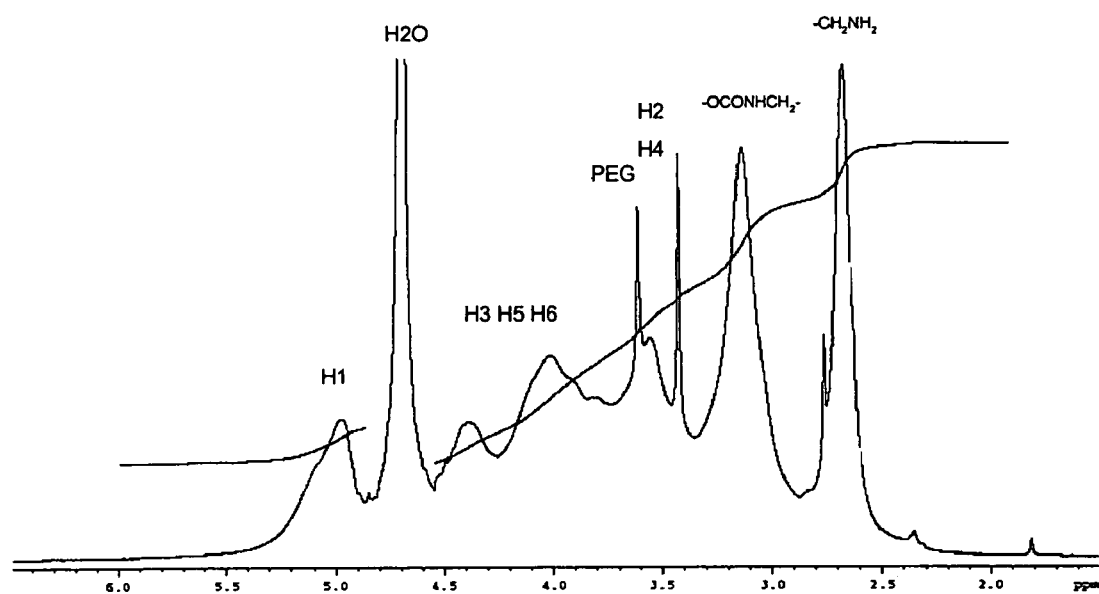
FIG. 4 shows The 1H NMR spectrum in D2O of the aminated polyrotaxane polycation disclosed in Example 2.

The CDI-activated polyrotaxane was dissolved in 40 ml of DMSO and added dropwise into a solution of 0.95 ml (14.17 mmol) of ethylene diamine in 40 ml of DMSO at room temperature and allowed to react overnight. The reaction mixture was poured into 900 ml of THF, centrifuged and washed with THF, and the resulting crude product was purified by column chromatography. Finally, 0.112 g orange solid was obtained (yield: 51%). FIG. 4 shows the 1H NMR spectrum of the aminated polyrotaxane (here called "APR-1").

Example 3

Preparation of Aminated Polyrotaxane with Alpha-Cyclodextrin Grafted with Pentaethylene-Hexamine Example 2 was repeated except that rather than use ethylene diamine 0.95 ml (14.17 mmol) pentaethylene-hexamine was used to aminate the polyrotaxane-1. The resulting aminated polyrotaxane is here called "APR-2".

Biological Study 1

Comparative Study of ARA-1, ARA-2 in Comparison with PEI and Cationic AaCD as Respective Positive and Negative Controls Preparation of Aminated Alpha-Cyclodextrin (AaCD) Grafted with Ethylene Diamine Alpha-cyclodextrin was activated with N,N'-carbonyldiimidazole (CDI), followed by amination by reaction with excess pentaethylene hexamine (PEHA). The products were purified using a G-50 Sephadex column to obtain the AaCD.

Table 1 below lists the data for the APR-1 and APR-2. For comparison, AaCD which is equivalent to the "monomer" of aminated polyrotaxanes and polyethylene imide (PEI) with a molecular weight of 25000, are also tabulated in Table 1.

and qualify of the purified plasmid DNA was assessed by optical density at 260 and 280 nm and by electrophoresis in 1% agarose gel. The purified plasmid DNA was resuspended in TE buffer (10 mM Tris-Cl, pH 7.5, 1 mM EDTA) and kept in aliquots at a concentration of 0.5 mg/ml.

Gel Retardation Experiments

Each polymer was examined for its ability to bind pRL-CMV through gel electrophoresis experiments. pRL-CMV (0.2 µg; 2 µl of a 0.1 µg/µl in TE buffer) was mixed with an equal volume of polymer at charge ratios between 0 and 10. Each solution was incubated for approximately 30 min at room temperature. For agarose gel electrophoresis, polymer DNA complexes mixed with a loading buffer were loaded onto an ethidium bromide containing 1% agarose gel. Gel electrophoresis was run at room temperature in TAE buffer (40 mM Tris-acetate, 1 mM EDTA) at 100 V for 40 min. DNA bands were visualized by a UV (254 nm) illuminator.

Cells and Media

All cell lines were purchased from ATCC (Rockville, Md.) unless otherwise stated. BHK-21 cells were maintained in Dulbecco's Modified Eagle's Medium (DMEM) supplemented with 10% heat-inactivated fetal bovine serum, 100 units/mg penicillin, 100 µg/ml streptomycin at 37° C. in humidified 5% $Co_2$ containing atmosphere. MES-SA cells and SK-OV-3 cells were grown in McCoy's 5a medium with 1.5 mM L-glutamine supplemented with 10% fetal bovine serum. Media and supplements were purchased from Gibco BRL (Gaithersburg, Md.).

In Vitro Transfection Protocol

For BHK-21 cells, transfections were carried out in triplicate under both serum-free condition and serum conditions with 20,000 cells per well in 0.5 ml DMEM medium containing 10% FBS that were previously seeded in 24-well tissue

TABLE 1

Molecular characteristics of aminated polyrotaxanes in comparison with aminated alpha-CD and PEI as controls.

| Gene carrier | Chemical composition | Average number of α-CD threaded | Amination agent | Average grafting number per glucose unit | Molecular Weight | MW/NH$_2$ |
|---|---|---|---|---|---|---|
| AaCD | Aminated α-CD with grafted PEHA | — | Pentaethylenehexamine | 1.0 | 2550 | 83 |
| APR-1 | Aminated Polyrotaxane-1 | 14.4 | Ethylenediamine | 0.86 | 24160 | 325 |
| APR-2 | Aminated Polyrotaxane-2 | 12.1 | Pentaethylenehexamine | 0.80 | 28280 | 109 |
| PEI | Poly(ethyleneimine) (Branched) | — | — | — | 20000 | 43 |

The gene carrier properties of the ARA-1, ARA-2, AaCD, and PEI listed in Table 1 above were compared in cell culture systems and will be described further below. Aminated alpha-CD was used as a negative control in the experiments and PEI as a positive control Plasmid DNA The plasmid DNA used was PRL-CMV (Promega, USA), encoding Renilla luciferase, which was originally cloned from the marine organism Renilla reniformis. All plasmid DNAs were amplified in E. coli and purified according to the supplier's protocol (Qiagen, Hilden, Germany). The quantity culture plates and grown for 24 hours at 37 C. The serum used in the following experiments was heat-inactivated fetal bovine serum (FBS) purchased from Gibco BRL (Gaithersburg, Md.).

The polymer/DNA complexes were prepared 30 minutes before transfection to stabilize the particles. The PEI/DNA complexes were prepared in the same method as the positive control. 1 µg of PRL-CMV per well was used for the transfection. pRL-CMV and the desired amount of polymer or PEI were diluted separately in 5% glucose solution to the equal volume. The PEI used (Sigma-Aldrich, St Louis, Mo., USA)

had a weight-average molecular weight (Mw) of approximately 25000 Da. The appropriate amount of polymer and PEI as added into DNA solutions drop by drop and the mixtures were vortexed and incubated for 30 min at room temperature before the transfection. Four hours later, the medium was discarded and changed with 500 μl fresh DMEM with serum each well. Cells were lysed at 24 hours posttransfection, the cell lysates were collected and centrifuged. The supernatant was used for luciferase detection with *Renilla Luciferase* Assay kit (Promega, Cergy Pontoise, France) and a luminometer (Berthold Lumat LB 9507, Germany). Results are expressed as relative light units (RLUs) integrated over 10 seconds per milligram of cell protein lysate (RLU/mg protein) using the bicinchoninic acid assay (Bio-Rad, CA, USA).

For MES-SA cells, transfections were carried out in triplicate under both serum-free condition and serum condition with 50,000 cells per well in 0.5 ml McCoy's 5a medium with 1.5 mM L-glutamine supplemented with 10% fetal bovine serum that were previously seeded in 24-well tissue culture plates and grown for 24 hours at 37° C.

The polymer/DNA complexes were prepared 30 minutes before transfection to stabilize the particles. The PEI/DNA complexes were prepared in the same method as the positive control. 1 μg of pRL-CMV per well was used for the transfection. pRL-CMV and the desired amount of polymer or PEI were diluted separately in 5% glucose solution to the equal volume. The PEI used (Sigma-Aldrich, St Louis, Mo., USA) had a weight-average molecular weight (Mw) of approximately 25000 Da. The appropriate amount of polymer and PEI as added into DNA solutions drop by drop and the mixtures were vortexed and incubated for 30 min at room temperature before the transfection. Four hours later, the medium was discarded and changed with 500 μl fresh McCoy's 5a serum each well. Cells were lysed at 24 hours posttransfection, the cell lysates were collected and centrifuged. The supernatant was used for luciferase detection with *Renilla Luciferase* Assay kit (Promega, Cergy Pontoise, France) and a luminometer (Berthold Lumat LB 9507, Germany). Results are expressed as relative light units (RLUs) integrated over 10 seconds per milligram of cell protein lysate (RLU/mg protein) using the bicinchoninic acid assay (Bio-Rad, CA, USA).

MTT-Based Cytotoxicity Assay

BHK-21 cells were seeded into 96-well microtiter plates (Nunc, Wiesbaden, Germany) at a density of 1×104 cells/well. After 24 h, culture media was replaced with serum-supplemented culture media containing serial dilutions of polymer extracts and the cells were incubated for 24 h. 20 μl sterile filtered MTT (5 mg/ml) stock solution in PBS was added to each well, reaching a final concentration of 0.5 mg MTT/ml. After 4 h, the supernatant was removed and formed formazan crystals were dissolved in 200 μl/well DMSO and measured spectrophotometrically in an microplate reader (Spectra Plus, TECAN) at a wavelength of 570 nm.

Six wells were treated together as a group. The relative cell growth (%) related to control wells without polymer was calculated by the following equation (A=absorbance at 570 nm):

Relative cell growth Rate=[$A$]test/[$A$]control×100

DNA Condensing Capability of the Aminated Polyrotaxanes

The ARA-1, ARA-2 and AaCD were examined for their abilities to condense plasmid DNA pRL-CMV through gel electrophoresis experiments in which pRL-CMV (0.2 μg/well) condensed in CYP25 nanoparticles with different N/P ratios using 1% agarose gel (DNA was visualized by ethidum bromide staining) Voltage: 100V Time: 40 mins.

Figure 5:
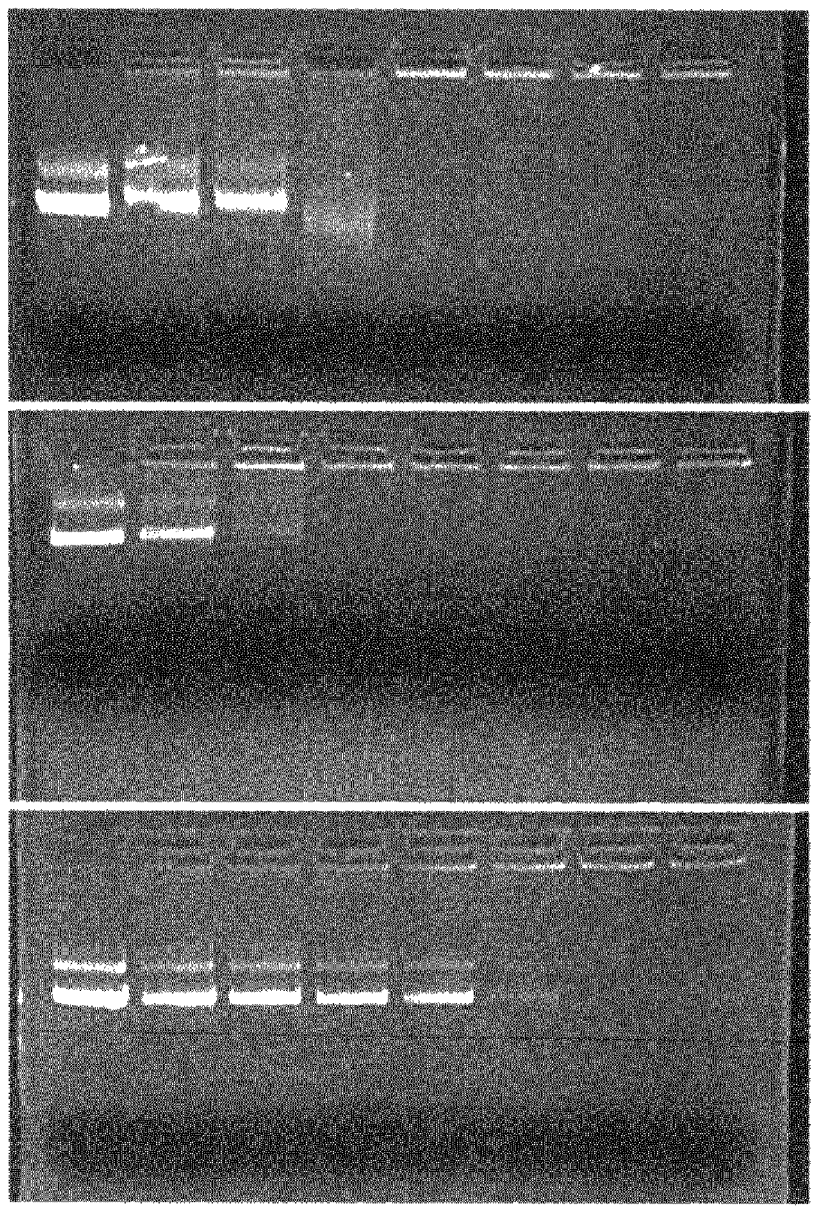
FIG. 5. is a picture of the electrophoretic mobility of plasmid DNA in cationic polymer/DNA complexes with different N/P ratios.

FIG. 5 shows the electrophoretic mobility of plasmid DNA in cationic polymer/DNA complexes with different N/P ratios for AaCD (FIG. 3A), APR-1 (FIG. 3B), and APR-2 (FIG. 3C).

It can been seen that AaCD condensed and neutralized pRL-CMV at and above a charge ratio of 2.5. APR-1 showed a stronger DNA condensation capability, and the same nucleic acid was neutralized at an N/P ratio of 2. APR-2 could condense the same plasmid at an N/P ratio 3.5.

Cytotoxicity Studies

Figure 6:
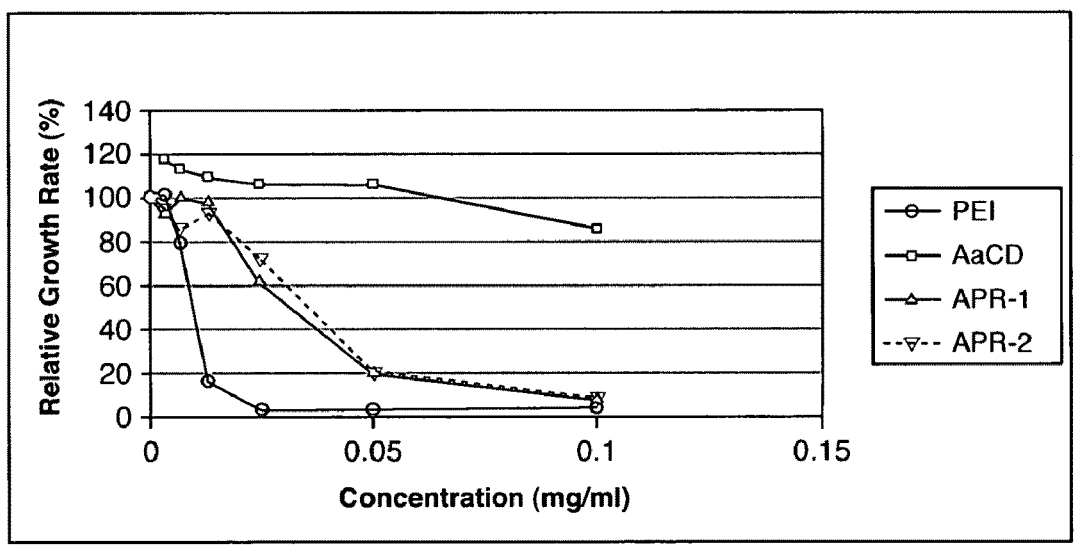
FIG. 6. shows cytotoxicity profiles of the aminated polyrotaxanes of examples 1 and example 2 in comparison with negative and positive controls.

Inhibition of BHK-21 cell growth by polymer extracts and the extracts dilutions after an incubation time of 1 day were examined, and the results are shown in FIG. 6. The results of the cytotoxicity assays show that the synthesized ARA-1 and ARA-2 were significantly less toxic than PEI in BHK-21 cell lines.

Gene Transfection Efficiency of AaCD in MES-SA Cells in Comparison with PEI

Figure 7:
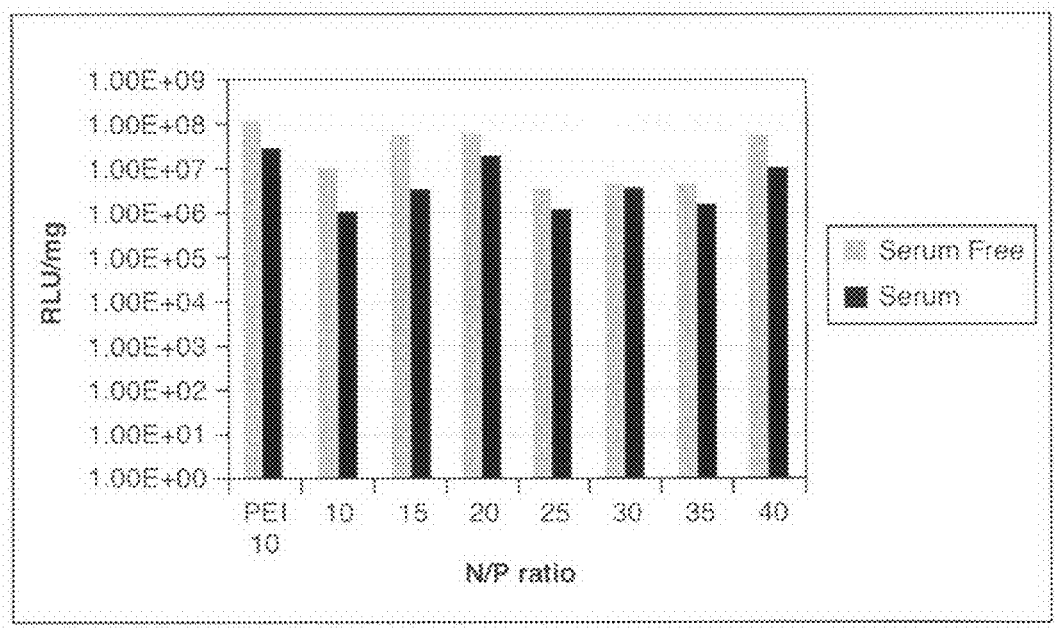
FIG. 7. shows a graph of the gene transfection efficiency of the negative control and positive control in MES-SA cells in the absence and presence of serum.

FIG. 7 shows the results of gene transfection efficiency of AaCD in MES-SA cells in comparison with PEI, in the absence and presence of serum. The luciferase assay demonstrated that the transfection efficiency of AaCD is lower than PEI under both serum and serum-free conditions.

Gene Transfection Efficiency of APR-1 in MES-SA Cells in Comparison with PEI

Figure 8:
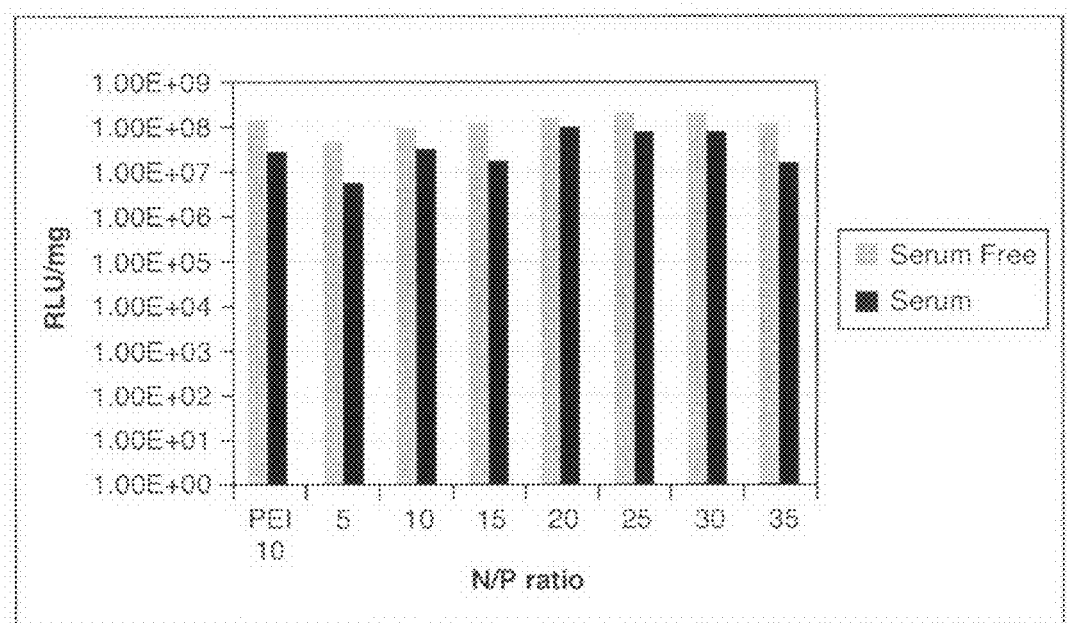
FIG. 8. shows a graph of the gene transfection efficiency of the polycation of example 1 in MES-SA cells in comparison with the positive control of example 3, in the absence and presence of serum.

FIG. 8 shows the results of the gene transfection efficiency of APR-1 in MES-SA cells in comparison with PEI, in the absence and presence of serum. The luciferase assay demonstrated that the transfection efficiency of APR-1 was higher than PEI in both serum free and serum conditions when the N/P ratio was in the range from 20 to 30.

Gene Transfection Efficiency of APR-2 in MES-SA Cells in Comparison with PEI

Figure 9:
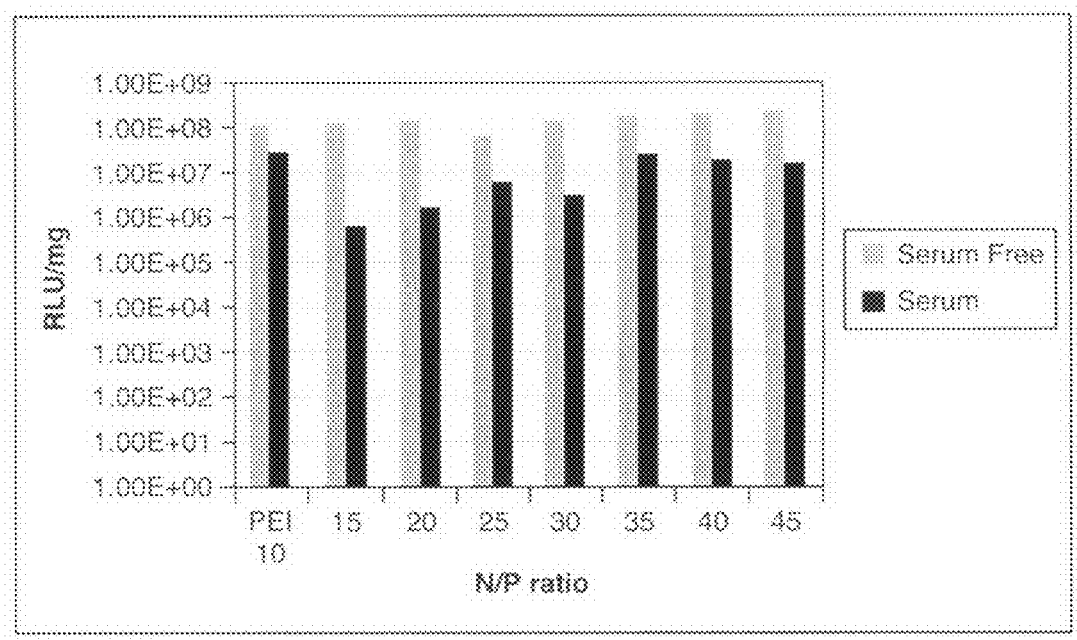
FIG. 9. shows a graph of the gene transfection efficiency of the polycation of example 2 in MES-SA cells in comparison with the positive control of example 3, in the absence and presence of serum.

FIG. 9 shows the results of the gene transfection efficiency of APR-2 in MES-SA cells in comparison with PEI, in the absence and presence of serum. The luciferase assay demonstrated that the transfection efficiency of APR-2 was higher than PEI in the absence of serum when the N/P ratio was in the range from 35 to 45. In serum condition, APR-2 shows similar transfection efficiencies to PEI at N/P ratio of 35.

Gene Transfection Efficiency of AaCD in BHK-21 Cells in Comparison with PEI

Figure 10:
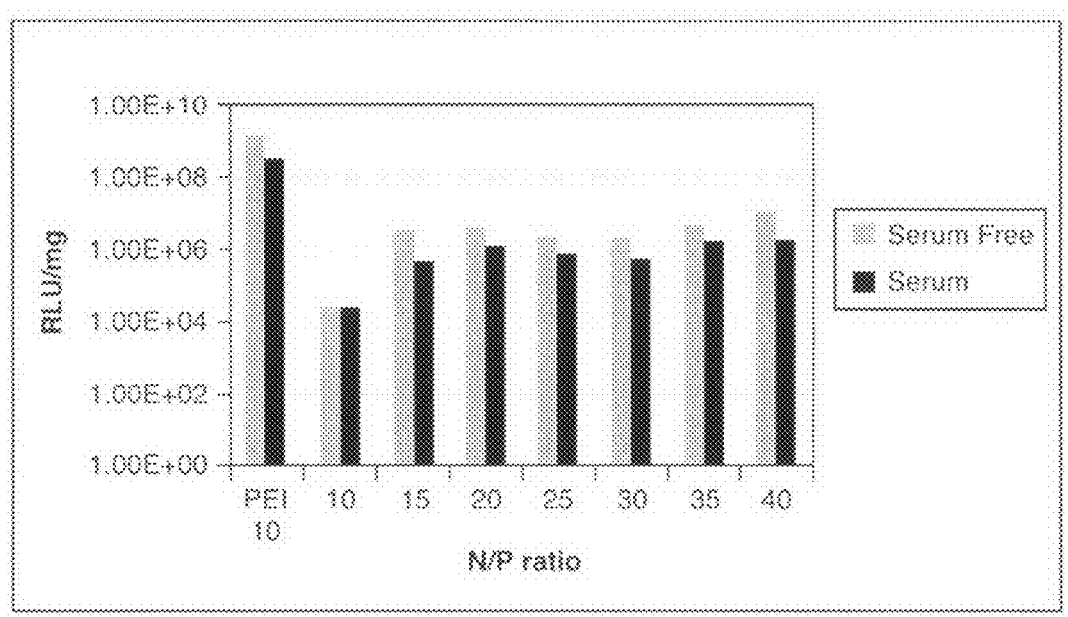
FIG. 10. shows a graph of the gene transfection efficiency of the negative control and positive control of comparative example 3 in BHK-21 cells in the absence and presence of serum.

FIG. 10 shows the results of the Gene transfection efficiency of AaCD in BHK-21 cells in comparison with PEI, in the absence and presence of serum. The luciferase assay demonstrated that the transfection efficiency of AaCD was lower than PEI under both serum and serum free conditions.

Gene Transfection Efficiency of APR-1 in BHK-21 Cells in Comparison with PEI

Figure 11:
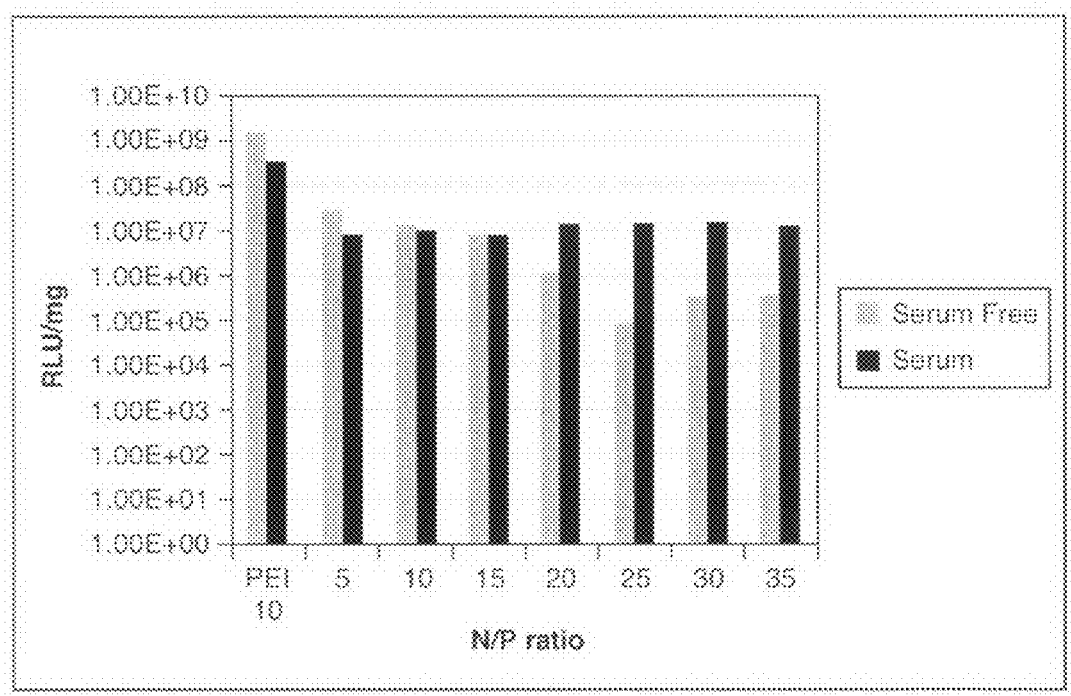
FIG. 11. shows a graph of the gene transfection efficiency of the polycation of example 1 in BHK-21 cells in comparison with the positive control of example 3, in the absence and presence of serum.

FIG. 11 shows the results of the gene transfection efficiency of APR-1 in BHK-21 cells in comparison with PEI, in the absence and presence of serum. The luciferase assay demonstrated that the transfection efficiency of APR-1 is lower than PEI under both serum and serum-free conditions.

Gene Transfection Efficiency of APR-2 in BHK-21 Cells in Comparison with PEI

Figure 12:
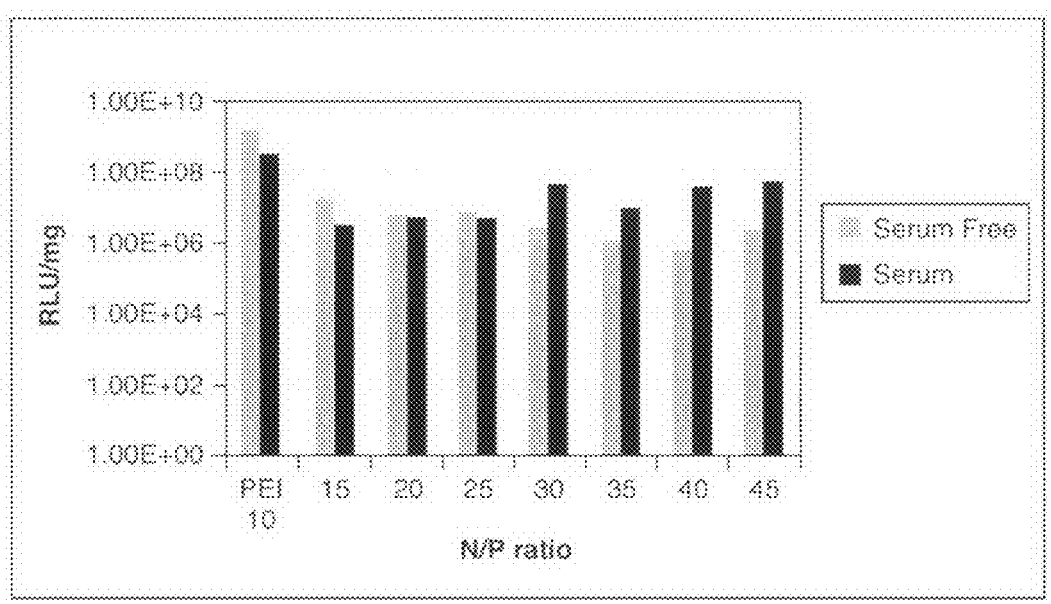
FIG. 12. shows a graph of the gene transfection efficiency of the polycation of example 2 in BHK-21 cells in comparison with the positive control of example 3, in the absence and presence of serum.

FIG. 12 shows the results of the gene transfection efficiency of APR-2 in BHK-21 cells in comparison with PEI, in the absence and presence of serum. The luciferase assay demonstrated that the transfection efficiency of APR-2 is lower than PEI under both serum and serum-free conditions.

Example 4

Preparation of Polyrotaxane ARA-3

Figure 13:
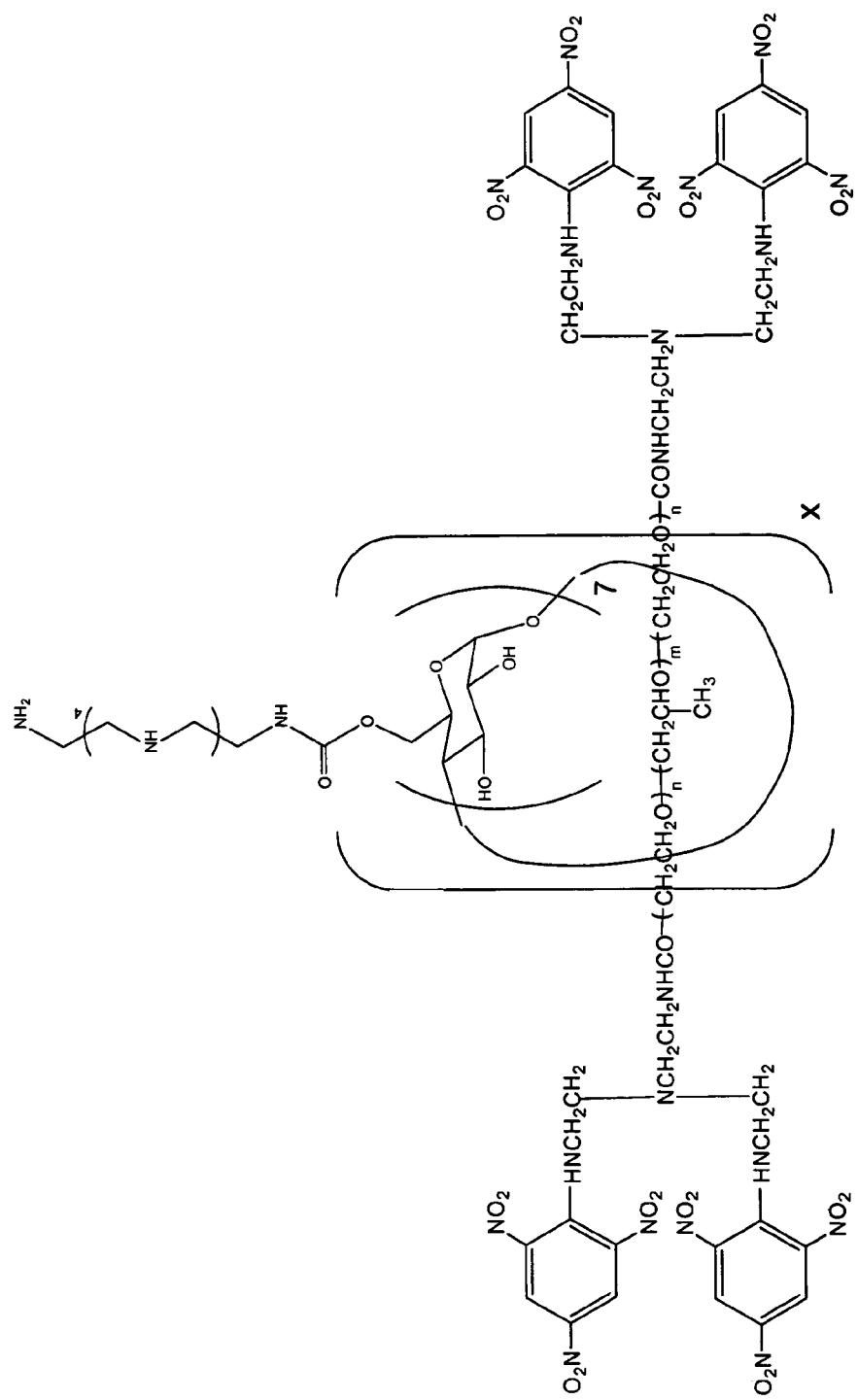
FIG. 13 shows a formula of a third synthesized aminated polyrotaxane cation.

Referring to FIG. 13, there is shown another aminated polysiloxane (ARA-3) which was used to transfect DNA to a target cell. The ARA-3 was synthesized using pluronic poly (ethylene oxide)-poly(propylene oxide)-poly(ethylene oxide) (PEO-PPO-PEO) triblock copolymer where, as shown in FIG. 13, m=30, n=13, and the molecular weight was 2,930. The PEO-PPO-PEO triblock copolymer was supplied by BASF (Germany). Picrylsulfonic acid solution and pentaethylenehexamine were purchased form Fluka & Riedel. The picrylsulfonic acid solution was neutralized with NaOH solution before use. Tris(2-aminoethyl)amine, anhydrous DMF and DMSO were obtained from Sigma-Aldrich. Alpha cyclodextrin ($\alpha$-CD) was purchased from Tokyo Kasei Inc.

DMSO-d6 used as solvent in the NMR measurements was also obtained from Sigma-Aldrich.

Figure 14:
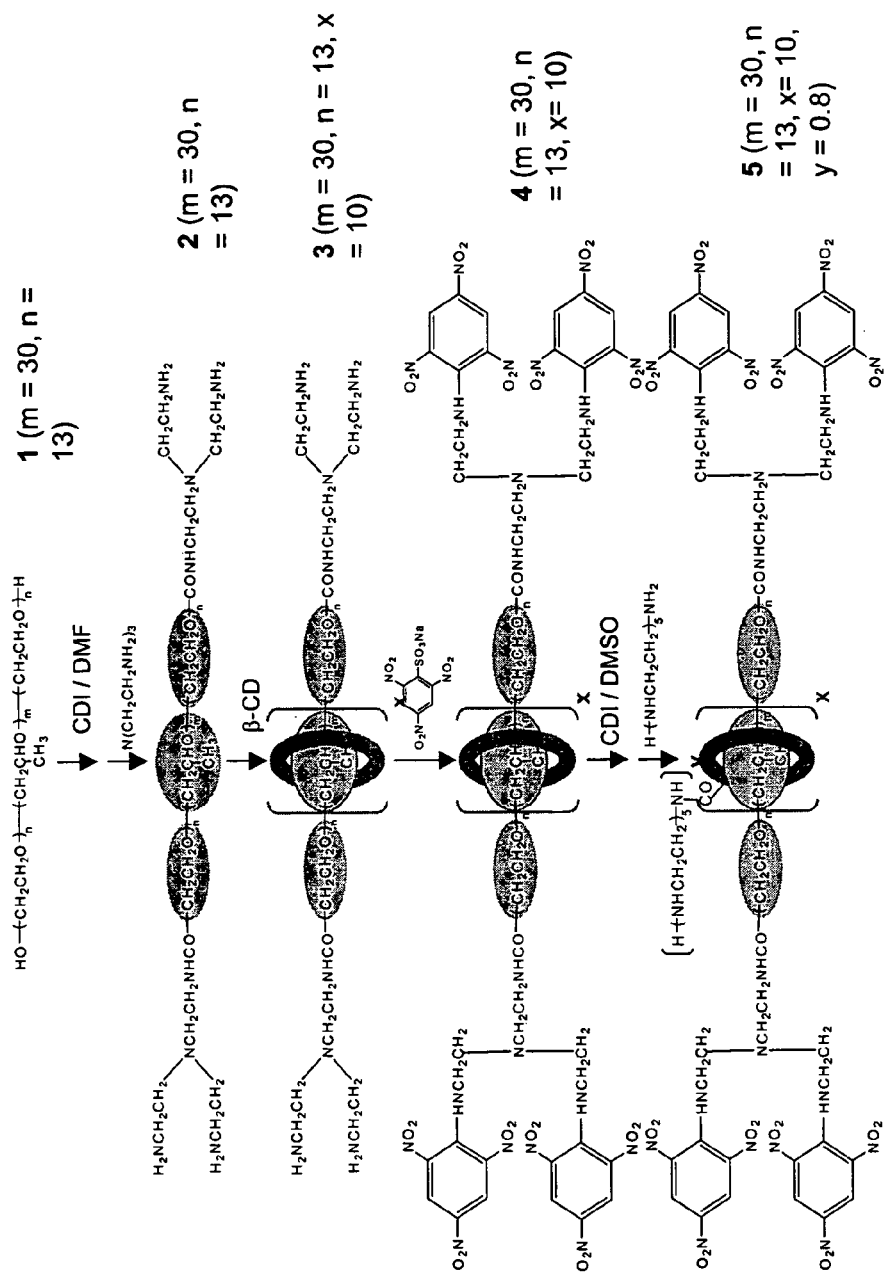
FIG. 14 shows the schema for synthesis of the aminated polyrotaxane cation shown in FIG. 13.

Referring to FIG. 14 there is shown the general schema for synthesis of ARA-3 from PEO-PPO-PEO triblock copolymer (1). The full synthesis of steps 1 to 5 will now be described. It should be noted that y is the ratio of a glucose unit to a cyclodextrin.

Synthesis Amino Terminated PEO-PPO-PEO (2): 2.99 g (1.02 mmol) PEO-PPO-PEO triblock copolymer was heated in a flask at 80° C. in vacuum overnight. When the flask cooled, 15 mL of anhydrous DMF was injected under nitrogen. The PEO-PPO-PEO triblock copolymer was dissolved by adding DMF solution dropwise during a period of 6 h under nitrogen to 15 mL of anhydrous DMF solution in which 1,1'-carbonyl-diimidazole (CDI) (1.65 g, 10.2 mmol) was dissolved, and the mixture was stirred overnight under nitrogen at room temperature. The resulting solution was slowly added dropwise during a period of 3 h into 15.538 g (102 mmol) of Tris(2-aminoethyl)amine which was dissolved in 15 mL of anhydrous DMF with stirring at room temperature, followed by stirring the mixture overnight. DMF was removed by vacuum evaporation, and the resulting solution was dissolved in $CHCl_3$ and washed with $H_2O$ for three times to remove excess Tris(2-aminoethyl)amine.

The solution was then concentrated to remove $CHCl_3$ and the resulting viscous solution was purified by size exclusion chromatography (SEC) on a Sephadex LH-20 column using methanol as eluent.

Finally, 2.3147 g viscous liquid was yielded (69.26%)(Step 2).

The $^1H$ NRM spectra for ARA-3 was as follows (400 MHz, DMSO-d6, 22° C.): $\delta$ 4.03 (m, 4H, $OCONCH_2$), 3.33-3.54 (m, 107H and 91H, —$CH_2CH_2O$— of PEO block and —$CH_2CHO$— of PPO block), 3.13 (m, 4H, $OCONCCH2$), 2.87 (m, 8H, CNCH2), 2.65 (m, 8H, $CH_2N$), 1.05 (d, 91H, —$CH_3$ of PPO block). Anal. Calcd for $C_{158}H_{322}N_8O_{60}.3H_2O$: C, 56.70; H, 9.88; N, 3.35. Found: C, 56.42; H, 9.94; N, 3.40.

Preparation of Polyrotaxane (3)

0.4 g the above amino-terminated PEO-PPO-PEO triblock copolymer was added to 266 mL $\beta$-CD saturated solution (0.03 g $\beta$-CD/mL $H_2O$) (3), and 0.6 g $NaHCO_3$ was added to adjust the pH value of the solution. The reaction mixture was ultrasonicated for 20 min and stirred at room temperature overnight. Then, 3.36 g sodium salt of picrylsulfonic acid was added and stirred overnight. 200 ml $H_2O$ was then poured into the reaction mixture to precipitate the product.

The precipitate was centrifuged and washed with water for three times. The resulting wet solid was dissolved in 30 ml DMSO and poured into 450 ml MeOH to precipitate the product. The precipitate was centrifuged and washed with MeOH for three times. The resulting wet solid was dissolved in 30 ml DMSO again and poured into 500 ml $H_2O$ to precipitate the product. The resulting precipitate was centrifuged and washed with $H_2O$ for 3 times. Finally, the resulting wet solid was freeze dried (liquid nitrogen) under vacuum. 0.2830 g pure polyrotaxane (4) was yielded (17.02%). The 1H NMR data (400 MHz, DMSO-d6, 22° C.) was as follows: $\delta$9.24 (s, 4H, meta H of phenyl), 8.93 (s, 4H, meta H of phenyl), 5.75 (s, 68H, O (2)H of CD), 5.70 (m 68H, O (3)H of CD), 4.83 (s, 68H, H(1)H of CD), 4.43 (d, 68H, O (6)H of CD), 3.00-4.00 (m, 340H, H(3), H(6), H(5), H(2) and H(4) of CD, 107H, —$CH_2CH_2O$— of PEO block, 91H, —$CH_2CHO$— of PPO block), 1.04 (m, 91H, —$CH_3$ of PPO block). Anal. Calcd for $C_{590}H_{1005}N_{20}O_{423}.42H_2O.5DMSO$: C, 44.19; H, 6.92; N, 1.72. Found: C, 43.62; H, 6.86; N, 1.69.

Preparation of Aminated Polyrotaxane (5)

The resulting polyrotaxane of step (4) (0.1513 g, 0.01 mmol) was dried at 40° C. in vacuum overnight. When the flask cooled, 40 mL dry DMSO was injected under nitrogen. After all 4 was dissolved, the DMSO solution of 4 was added dropwise during a period of 6 h under nitrogen to 40 mL of anhydrous DMSO solution in which 1,1'-carbonyl-diimidazole (CDI) (1.654 g, 10.2 mmol) was dissolved, and the mixture was stirred overnight under nitrogen at room temperature. Then, the mixture of 300 ml THF and 600 ml $Et_2O$ was poured in the resulting solution to precipitate the product. The precipitate was centrifuged and washed with THF for 3 times. Then, the resulting wet solid was dissolved in 40 mL DMSO and this solution was slowly added dropwise during a period of 3 h into 3.56 mL (12.24 mmol) of pentaethylenehexamine which was dissolved in 40 mL of DMSO with stirring at room temperature, followed by stirring the mixture overnight. 900 mL THF was poured in the reaction mixture to precipitate the product. The precipitate was centrifuged and washed with THF for 3 times, and the resulting crude product was purified by size exclusion chromatography (SEC) on a Sephadex G-50 column using DI water as eluent. Finally, 0.1562 g brown solid 5 was yielded (55.01%). 1H NMR (400 MHz, D2O, 22☐): $\delta$ 8.48 (s, 4H, meta H of phenyl), 8.01 (s, 4H, meta H of phenyl), 5.02 (d, broad, 68H, H(1)H of CD), 3.00-4.62 (m, broad, 324H, H(3), H(6), H(5), H(2) and H(4) of CD, 101H, —$CH_2CH_2O$— of PEO block, 45H, —$CH_2CHO$— of PPO block, 103H, $CONCH_2$ of pentaethylenehexamine), 2.69 (m, 1232H, $NCH_2$ of pentaethylenehexamine), 1.09 (m, 91H, —$CH_3$ of PPO block). Anal. Calcd for $C_{1102}H_{2339}N_{328}O_{475}.60H_2O$: C, 45.87; H, 8.59; N, 15.91. Found: C, 45.19; H, 7.99; N, 16.01.

The produced ARA-3 of Step 5 of FIG. 14 is shown in FIG. 13.

Biological Study 2 of ARA-3

The same assays as outlined above under "Biological Study 1" were repeated on the ARA-3, except that PC3 cells and Cos7 cells were used in this study. Hereafter, ARA-3 are referred to as CYP25.

Figure 15:
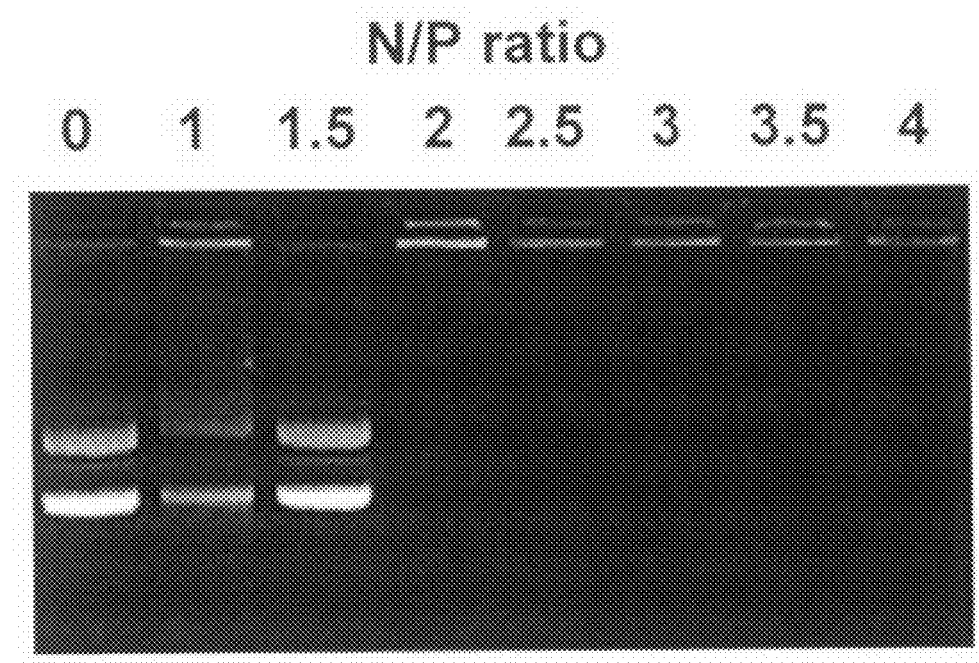
FIG. 15 shows a picture of the electrophoretic mobility of plasmid DNA complexed with the aminated polyrotaxane cation shown in FIG. 13.

Referring to FIG. 15. there is shown electrophoretic mobility of plasmid PRL-CMV (0.2 µg/well) condensed in CYP25 nanoparticles with different N/P ratios using 1% agarose gel (DNA was visualized by ethidum bromide staining) Voltage: 100VTime: 40 mins.

It can be seen that the CYP25 condensed and neutralized pRL-CMV at and above a charge ratio of 2.

Figure 16:
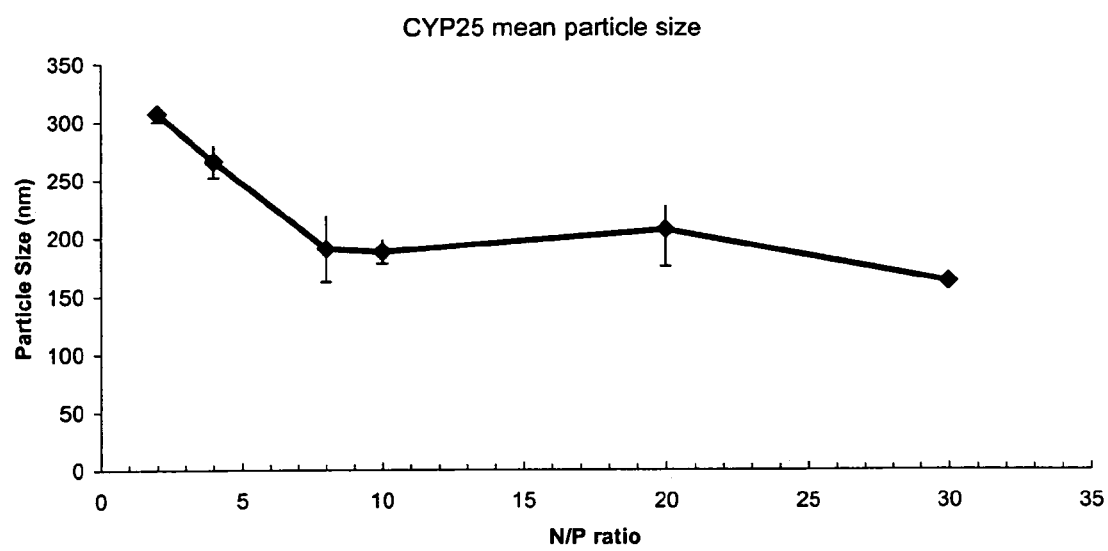
FIG. 16 shows the particle size of the aminated polyrotaxane cation shown in FIG. 13 at various N/P ratios.

FIG. 16 shows the particle size of CYP25/DNA complexes at different N/P ratios. 100 ng of pRL-CMV plasmid were complexed with CYP25 at various N/P ratios in a total volume of 1 ml. The complexes were allowed to stabilize at room temperature for 30 minutes before analysing with a Zeta Plus zeta potential analyzer.

Figure 17:
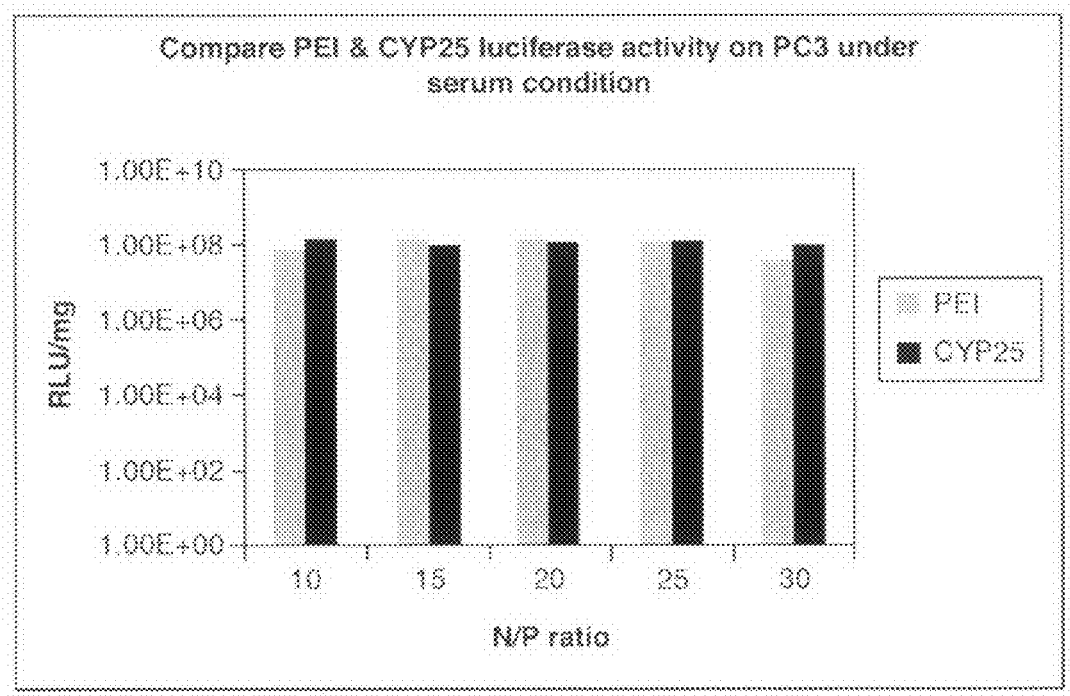
FIG. 17 shows Luciferase activities of PC3 cells by the aminated polyrotaxane cation shown in FIG. 13.

FIG. 17 shows Luciferase activities of PC3 cells by CYP25. Transfection of PRL-CMV plasmid condensed by PEI and CYP25 were shown for comparison with the presence of serum. Transfection was carried out on PC3 cells at of 2 μg of PRL-CMV per well in the presence of serum for 4 h at 37° C. per well of 24-well plate. After that the cells were allowed to rest an extra 72 h, and then harvested for the measurement of the luciferase activity.

The data were expressed in relative luciferase units normalized for protein content.

It can be seen that CYP25 had close luciferase activity as PEI (MW 25000) at N/P ratios of between 10-25. At an N/P ratio above 30, the CYP25 was higher.

Figure 18:
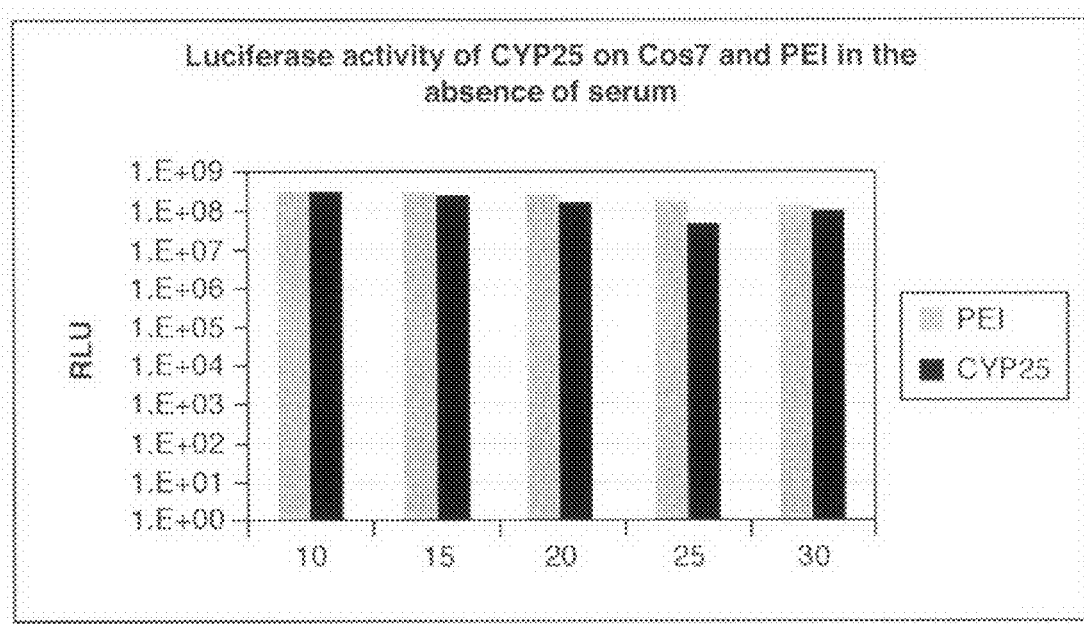
FIG. 18 shows luciferase activities of Cos7 cells by the aminated polyrotaxane cation shown in FIG. 13 in the absence of serum.

FIG. 18 shows luciferase activities of Cos7 cells by CYP25. Transfection of PRL-CMV plasmid condensed by PEI and CYP25 were shown for comparison in the absence of serum. Transfection was carried out on Cos7 cells at 1 μg of pRL-CMV per well in the presence and absence of serum for 4 h at 37° C. per well of 24-well plate. After that cells were allowed to rest an extra 72 h, and then harvested for the measurement of the luciferase activity. The data were expressed in relative luciferase units normalized for protein content.

It can be seen that CYP25 had close luciferase activity as PEI (MW 25000) at N/P ratios of between 10-15.

Figure 19:
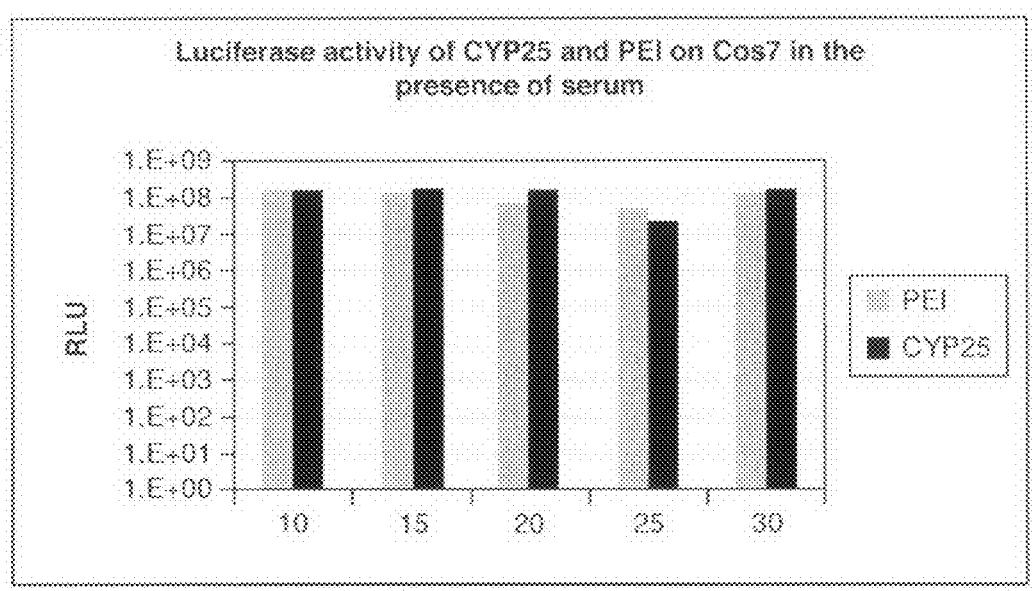
FIG. 19 shows luciferase activities of Cos7 cells by the aminated polyrotaxane cation shown in FIG. 13 in the presence of serum 13CYP25.

FIG. 19 shows luciferase activities of Cos7 cells by CYP25. Transfection of PRL-CMV plasmid condensed by PEI and CYP25 were shown for comparison in the presence of serum. Transfection was carried out on Cos7 cells at of 1 μg of pRL-CMV per well in the presence and absence of serum for 4 h at 37° C. per well of 24-well plate. After that cells were allowed to rest an extra 72 h, and then harvested for the measurement of the luciferase activity. The data were expressed in relative luciferase units normalized for protein content.

APPLICATIONS

Advantageously, the disclosed supramolecular polycations can be used to deliver DNA to target cells. Accordingly, the disclosed polycations can be used in such applications as gene therapy and DNA vaccination for the treatment and control of diseases.

Advantageously, the disclosed polycations provide a useful non-viral vector system for DNA delivery to target cells. The disclosed polycations therefore may avoid one or more of the problems associated with viral vectors delivery systems, including high toxicity, restricted targeting of cells, limited DNA carrying capacity, production and packaging problems, recombination, and high cost.

Advantageously, the disclosed polycations may be easy to use and to manufacture on a large-scale.

Advantageously, the disclosed polycations may be a useful substitute to PEI. More advantageously, the disclosed polycations have low to no cytotoxicity relative other non-viral DNA delivery systems, such as PEI while having high transfection activity.

Advantageously, the disclosed polycations are biodegradable and therefore avoid damage of the cells after the gene delivery. It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A supramolecular polycation assembly capable of forming a complex with a nucleic acid for carriage thereof, the supramolecular polycation assembly comprising:

at least one amino-substituted cyclodextrin having a cavity extending therethrough, wherein the amino-substituted cyclodextrin comprises one or a plurality of aminated D-glucose units of the formula:

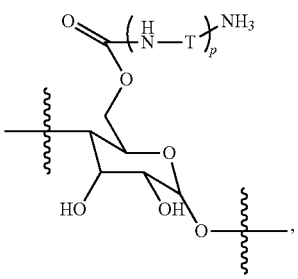

wherein:
p is an integer from 0 to 8; and
T is optional and is an alkyl selected from the group consisting of methyl, ethyl and propyl;
a co-polymer backbone threaded into the cavity of the cyclodextrin; and
a pair of bulky moieties capping the terminals of the co-polymer backbone to inhibit dethreading of the cyclodextrin from the co-polymer backbone, wherein the net positive charge of the supramolecular polycation assembly enables a complex to form with the nucleic acid.

2. The supramolecular polycation assembly of claim 1, wherein the bulky moieties are biocleavable.

3. The polycation of claim 1, wherein the co-polymer backbone has a shape selected from the group consisting of linear polymers, branched polymers, star polymers and combinations thereof.

4. The supramolecular polycation assembly of claim 1, wherein a polymer of the co-polymer backbone is selected from the group consisting of polyethylene glycol, polypropylene glycol, polybutylene glycol, polypentylene glycol, polyhexylene glycol, polymethyl vinyl ether, polyethyl vinyl ether, polyisoprene, polyisobutylene, and polybutadiene.

5. The supramolecular polycation assembly of claim 1, wherein the co-polymer backbone has a molecular weight in the range selected from the group consisting of 200 to 50000, 200 to 10000, 200 to 5000, and 200 to 2000.

6. The supramolecular polycation assembly of claim 1, wherein a plurality of cyclodextrin compounds are threaded on the co-polymer backbone.

7. The supramolecular polycation assembly of claim 1, wherein the bulky moieties are either one of a group having at least one benzene ring or a group having at least one tertiary butyl.

8. The supramolecular polycation assembly of claim 1, wherein the co-polymer backbone is a straight chain co-polymer and the bulky moieties are connected to the straight chain co-polymer backbone by a biocleavable linker.

9. The supramolecular polycation assembly of claim 8, wherein the biocleavable linker is selected from the group consisting of amides, amines, alkyls having from 1 to 8 carbon atoms, esters having from 1 to 8 carbon atoms, anhydrides and combinations thereof.

10. A method for introducing an exogenous nucleic acid molecule into a target cell comprising the steps of: (a) forming a complex between a polycation as claimed in claim 1 and a nucleic acid; and (b) introducing the formed complex into a target cell in vitro.

11. The supramolecular polycation assembly of claim 1, wherein the co-polymer backbone comprises polyethylene glycol and polypropylene glycol.

12. The supramolecular polycation assembly of claim 1, wherein p is 1 to 4.

13. The supramolecular polycation assembly of claim 1, wherein p is 5.

14. The supramolecular polycation assembly of claim 1, wherein T is ethyl.

* * * * *